(12) United States Patent
Meyer et al.

(10) Patent No.: US 8,128,229 B2
(45) Date of Patent: Mar. 6, 2012

(54) RNFL MEASUREMENT ANALYSIS

(75) Inventors: Scott A. Meyer, Livermore, CA (US); Mary K. Durbin, San Francisco, CA (US); Paul F. Stetson, Piedmont, CA (US); Bagrat Amirbekian, Pleasanton, CA (US)

(73) Assignee: Carl Zeis Meditec, Inc., Dublin, CA (US)

( * ) Notice: Subject to any disclaimer, the term of this patent is extended or adjusted under 35 U.S.C. 154(b) by 0 days.

(21) Appl. No.: 12/859,727

(22) Filed: Aug. 19, 2010

(65) Prior Publication Data

US 2011/0063573 A1    Mar. 17, 2011

Related U.S. Application Data

(63) Continuation of application No. 12/207,303, filed on Sep. 9, 2008, now Pat. No. 7,798,647.

(60) Provisional application No. 60/994,172, filed on Sep. 18, 2007, provisional application No. 61/046,311, filed on Apr. 18, 2008.

(51) Int. Cl.
*A61B 3/10* (2006.01)

(52) U.S. Cl. .................. 351/205; 351/206; 351/246

(58) Field of Classification Search .................. 351/200, 351/202, 205, 206, 210, 221, 246
See application file for complete search history.

(56) References Cited

U.S. PATENT DOCUMENTS 5,321,501 A    6/1994  Swanson et al.
(Continued)

OTHER PUBLICATIONS

De Boer, J. F. et al. (Mar. 1, 1999). "Determination of the Depth-Resolved Stokes Parameters of Light Backscattered From Turbid Media by Use of Polarization-Sensitive Optical Coherence Tomography," *Optics Letters* 24(5): 300-302.

(Continued)

*Primary Examiner* — Huy K Mai
(74) *Attorney, Agent, or Firm* — Morrison & Foerster LLP

(57) ABSTRACT

One embodiment of the present invention accounts for individual anatomical variation when evaluating optical nerve fiber measurements. In one aspect, contextual information is used to compensate or correct measurement data. In another aspect, reference coordinates are remapped for improved comparison or visualization. In one embodiment of this latter aspect, the method uses measurements of nerve fiber capacity and maps of nerve fiber retinal service to improve sensitivity and specificity in eye function metrics. In one instance, we use the birefringence of nerve fibers to determine the orientation of the fibers within the RNFL. Orientation of the fibers about the ONH is indicative of the service provided by the fibers and is used to improve the interpretation of thickness measurements of the nerve fiber layer. Normalized nerve fiber measurements about the optic nerve head improve specificity and sensitivity as compared to the standard model. These improvements are a result of partitioning the normative database or modifying the measurement data prior to comparison. Statistics on normalized measurements of nerve fiber bundles also show improvements in specificity and sensitivity.

25 Claims, 8 Drawing Sheets

U.S. PATENT DOCUMENTS

| | | | |
|---|---|---|---|
| 5,459,570 | A | 10/1995 | Swanson et al. |
| 5,485,229 | A | 1/1996 | Hare |
| 5,787,890 | A | 8/1998 | Reiter et al. |
| 6,208,415 | B1 | 3/2001 | De Boer et al. |
| 6,356,036 | B1 | 3/2002 | Zhou |
| 6,385,358 | B1 | 5/2002 | Everett et al. |
| 6,927,860 | B2 | 8/2005 | Podoleanu et al. |
| 7,016,048 | B2 | 3/2006 | Chen et al. |
| 7,301,644 | B2 | 11/2007 | Knighton et al. |
| 2008/0100612 | A1 | 5/2008 | Dastmalchi et al. |
| 2008/0312552 | A1 | 12/2008 | Zhou et al. |
| 2009/0033868 | A1* | 2/2009 | Huang et al. ............ 351/205 |

OTHER PUBLICATIONS

Dreher, A. W. et al. (Jul. 1, 1992). "Spatially Resolved Birefringence of the Retinal Nerve Fiber Layer Assessed With a Retinal Laser Ellipsometer," *Applied Optics* 31(19):3730-3735.

Fitzgibbon, T. et al. (1996). "Retinotopy of the Human Retinal Nerve Fibre Layer and Optic Nerve Head," *The Journal of Comparative Neurology* 375:238-251.

Frangi, A. et al. (Oct. 1999). "Model-Based Quantitation of 3D Magnetic Resonance Angiographic Images," *IEEE Transactions on Medical Imaging* 18(10):946-956.

Garway-Heath, D.F. et al. (Oct. 2000). "Mapping the Visual Field to the Optic Disc in Normal Tension Glaucoma Eyes," *Ophthalmology* 107(10):1809-1815.

Hitzenberger, C. K. et al. (Dec. 17, 2001). "Measurement and Imaging of Birefringence and Optic Axis Orientation by Phase Resolved Polarization Sensitive Optical Coherence Tomography," *Optics Express* 9(13):780-790.

Hood, D. C. et al. (2007). "A Framework for Comparing Structural and Functional Measures of Glaucomatous Damage," *Progress in Retinal & Eye Research* 26:688-710.

Hood, D. C. et al. (Aug. 2007). "Structure versus Function in Glaucoma: An Application of a Linear Model," *Investigative Ophthalmology & Visual Science* 48(8):3662-3668.

Hood, D. C. et al. (2008). "The Location of the Temporal Retinal Veins and Arteries Can Be Used to Improve the Sensitivity of the Retinal Nerve Fiber Layer Thickness Measured With Optical Coherence Tomography (OCT)," *Investigative Ophthalmology & Visual Science* 49:E-Abstract 3765, 2 pages.

Jonas, J. B. et al. (Oct. 1991). "Parapapillary Atrophy and Retinal Vessel Diameter in Nonglaucomatous Optic Nerve Damage," *Investigative Ophthalmology & Visual Science* 32(11):2942-2947.

Jonas, J. B. et al. (1994). "Shape of the Neuroretinal Rim and Position of the Central Retinal Vessels in Glaucoma," *British Journal of Ophthalmology* 78:99-102.

Knighton, R. W. et al. (2002). "Analytical Model of Scanning Laser Polarimetry for Retinal Nerve Fiber Layer Assessment" *Investigative Ophthalmology & Visual Science* 43(2):383-392.

MacQueen, J. B. (1967). "Some Methods for Classification and Analysis of Multivariate Observations," *Proceedings of 5-th Berkeley Symposium on Mathematical Statistics and Probability*, University of California Press, pp. 281-297.

Park, B. H. (Oct. 1, 2005). "Optic Axis Determination Accuracy for Fiber-Based Polarization-Sensitive Optical Coherence Tomography," *Optics Letters* 30(19):2587-2589.

Rader, J. et al. (Jan. 1994). "Peripapillary Vasoconstriction in the Glaucomas and the Anterior Ischemic Optic Neuropathies," *American Journal of Ophthalmology* 117(1):72-80.

Roth, J. E. et al. (Jul. 1, 2001). "Simplified Method for Polarization Sensitive Optical Coherence Tomography," *Optics Letters* 26(14):1069-1071.

Sato, Y. et al. (1998). "Three Dimensional Multi-Scale Line Filter for Segmentation and Visualization of Curvilinear Structures in Medical Images," *Medical Image Analysis* 2(2):143-168.

Waldock, A. et al. (1998). "Clinical Evaluation of Scanning Laser Polarimetry: I. Intraoperator Reproducibility and Design of a Blood Vessel Removal Algorithm," *British Journal of Ophthalmology* 82:252-259.

\* cited by examiner

RNFL MEASUREMENT ANALYSIS

PRIORITY

This application is a continuation of U.S. patent application Ser. No. 12/207,303, filed Sep. 9, 2008, which in turn claims priority to U.S. Provisional Application Ser. No. 60/994,172, filed Sep. 18, 2007 and U.S. Provisional Application Ser. No. 61/046,311, filed Apr. 18, 2008, all of which are incorporated herein by reference.

TECHNICAL FIELD

The subject invention generally relates to eye evaluations. In particular, the invention accounts for individual anatomical variation when evaluating optical nerve fiber measurements.

BACKGROUND

For ease of exposition and understanding, the descriptions and examples presented herein relate to optical imaging of the retinal nerve fiber layer (RNFL). For those versed in the art it will be clear that the methods described apply equally well in other applications. In particular, the applications to RNFL thickness and orientation applies to other materials exhibiting orientation dependent form birefringence.

The retinal nerve fiber layer (RNFL) is formed by highly ordered optic nerve fiber bundles comprised of parallel axons containing small diameter cylindrical cell structures. The diameters of the cylindrical cell structures are smaller than the wavelength of light. These nerve cells transmit the visual signal generated by the photoreceptors along the optic nerve to the brain.

In glaucoma and certain other diseases, these nerve fibers can become damaged. Glaucoma is a term used to describe a group of diseases characterized by the loss of retinal ganglion cells and their axons and is one of the leading causes of blindness in the world. In many cases, vision loss due to glaucoma is irreversible. Glaucoma diagnosis is most commonly associated with an increase in intraocular pressure (TOP); however, diagnosis may also be based on the assessment of the optic nerve head (ONH), visual function, and/or the health and thickness of the RNFL. RNFL defects are early signs of glaucoma and frequently occur prior to measurable visual field loss. Since retinal function damage, at present, is irreversible, early detection and treatment are highly sought out for improved outcomes. The demonstrated high correlation between RNFL thickness and retinal function allows for early detection of potential retinal damage by means of retinal thickness measurements.

In recent years, scanning laser polarimetry (SLP) has demonstrated highly reliable indirect measurement of RNFL thickness. SLP uses a confocal scanning laser ophthalmoscope to measure retardation of the optical signal through the RNFL. The optical retardation is converted into thickness by means of a correlation that has been validated by histology. Under SLP imaging, the highly ordered, parallel fiber bundles of the RNFL show form-birefringence with the slow axis parallel to the direction of the fibers.

Another optical imaging technology is Optical Coherence Tomography (OCT). OCT has sufficient imaging resolution to measure the RNFL directly. Polarization sensitive (PS)-OCT can be used to also detect the optic axis of a sample. The optic axis can be determined using multiple interrogations of an RNFL region (de Boer, J. F. et al., *Optics Letters* 24: 300-302, Roth, J. E. et al., *Optics Letters* 26, 1069-1071) or the fast optic axis can be determined by use of a single A-scan (Hitzenberger, C. K. et al., *Optics Express,* 13, 780-790). In either case, PS-OCT can be used to determine fiber orientation within the RNFL.

Current SLP and OCT measures of NFL thickness are improving early detection of decreased eye function due to reductions in nerve tissue capacity. Still, there is a need for increased specificity and sensitivity of medical diagnosis from ophthalmological measurements.

SUMMARY

The present invention is defined by the claims and nothing in this section should be taken as a limitation on those claims. In one aspect, the invention improves specificity and sensitivity of measurements, by accounting for anatomical variations within the population.

In accordance with one aspect of the present invention, a method and apparatus is provided for improving the comparison of measurements of a first parameter to a normative database, a previous measurement of the same parameter, or another measured parameter. In one embodiment, the improvement is accomplished by measuring a second parameter at essentially the same location and using it to normalize the first parameter with respect to the comparison. The first parameter primarily discussed herein is nominally the thickness $t(r,\theta)$ of the retinal nerve fiber layer (RNFL) and the second parameter is nominally a reference coordinate used in displaying this thickness. In the prior art, this reference coordinate is the angle $\theta$ of the polar coordinate of the location of the thickness measurement. RNFL thickness is only a surrogate measure of the capacity of the nerve fiber layer (NFL). When using the thickness as a measure of capacity, one nominally assumes that each nerve fiber is essentially equivalent from subject to subject, so that capacity is proportional to thickness. For retinal thickness comparisons, measurements are taken around the optic nerve head (ONH), where the nerve fibers are closely packed into the limited space.

In one embodiment of the present invention, the reference coordinate of the RNFL thickness measurement is remapped before comparison or display. For example, in one specific embodiment, the reference coordinate is remapped to the orientation $o(r,\theta)$ of the nerve fiber bundles instead of the geometric angle $\theta$ of the measurement.

In another embodiment of the present invention, the reference coordinate of the RNFL thickness measurement is an adjustment of the geometric angle $\theta$ of the measurement. This adjustment is made using contextual information derived from the image data. Alternatively, the reference coordinate may be derived directly from the contextual information without regard to the geometric angle $\theta$. For example, one implementation of the present invention uses the thickness measurement of nerve fiber bundles themselves to create a reference coordinate.

Another embodiment of the present invention compares the current fiber bundle orientation at the ONH to a typical fiber bundle orientation at the ONH. This comparison is used to predict locations of decreased retinal function when regions of decreased RNFL thickness are observed. These regions can be correlated to other exams of the retina, such as visual field measurements.

Another embodiment of the present invention compares the current fiber bundle orientation in a region nearby the ONH to a typical fiber bundle orientation over a similar region. This region could be an annulus about the ONH, a wedge nearby the ONH or yet some other region such as the peripapillary region.

Yet another embodiment of the present invention uses the orientation of the nerve fiber bundles instead of the geometric angle of the measurement for computing post-processing statistics.

Yet another embodiment of the present invention uses the orientation of blood vessels to predict the orientation of nerve fiber bundles instead of measuring the orientation of the nerve fiber bundles directly.

DETAILED DESCRIPTION

Figure 1:
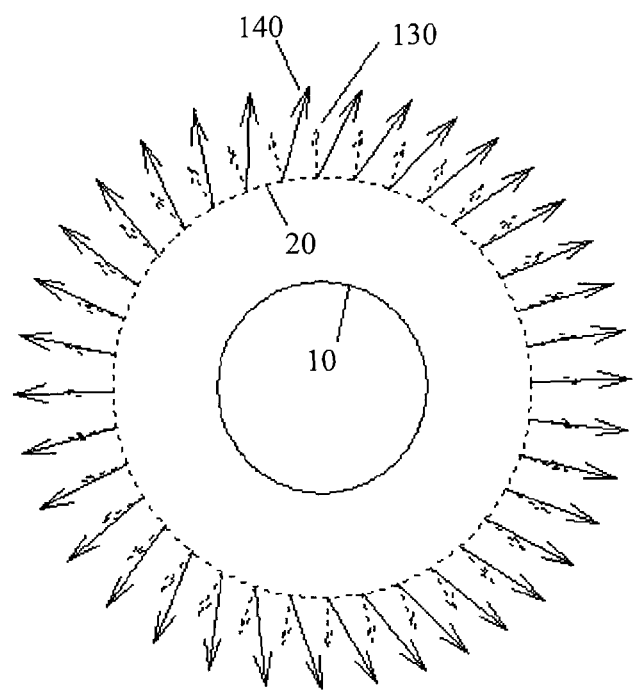
FIG. 1 is an illustration of the orientation of nerve fibers compared to a purely radial distribution.

The invention described herein improves the specificity and/or the sensitivity of measurements, by accounting for anatomical variations within the population. For example, when measuring optical nerve fiber or comparing such measurements to a normative database, accounting for anatomical variations reduces the variability of "normals". The methods described herein are improvements accounting for measurement variability based on individual anatomical variations of optical nerve fiber. These methods apply to the normative database, to the measurement data, or to measurements computed from the measurement data. Methods applied to data may apply to the data itself or the reference coordinates of the data being measured. The comparison to the normative database may be used for an analysis of structure, an assessment of structure and visual function, and/or an assessment of the progression. Progression assessment evaluates structural and/or functional change over time.

One method applied to the database itself partitions the database into sets of subjects who share anatomical similarity, and then determines which of these partitions evaluates the patient most appropriately.

Specialized databases for race, age, sex and other discriminators reduce the variability within the classes, providing greater specificity and sensitivity by reducing the variability amongst normals. Alternatively, a single database can be partitioned into known classes. Alternatively, the database of normals may be partitioned using a clustering classifier, such as k-means clustering, to identify clustering patterns within the database without regard to previously defined classes. For a description of k-means clustering, please see MacQueen's U. of Cal. Press publication, cited below. Indeed, improvements in specificity and/or sensitivity can be achieved by partitioning the database, compensating the measurements, or remapping the measurements to reduce variability within the normal range.

Alternatively, the anatomically corrected reference coordinate may be derived directly from measurements and contextual information. Contextual information accounting for individual anatomical variations may include age, ethnicity, or other demographic information, but must include one or more contextual measurements of anatomy or parameters derived from those measurements before we can extract a corrected reference. The anatomical contextual information may be gathered from the same measurement data used for the nerve fiber bundle measurements or from other sources. These other sources may include other OCT images, SLP images, or other types of images, such as a fundus photograph or images from a scanning ophthalmoscope. The anatomical contextual information may also include measurements such as axial length of the eye or the subject's optical power or corrective lens prescription.

Measurements of optical nerve fiber bundles provide anatomical context if the distribution of the thickness is compared to other patterns of thickness from the database of normal subjects. The location or thickness of major bundles of nerve fiber, for example, may be used as inputs to determine the categorization, compensation, or re-mapping of the measurements of optical nerve fiber. Other anatomical context from OCT scans may include analyses of size or locations of blood vessels, analyses of size, shape, or orientation of the ONH, measurements of the distance between the ONH and the fovea, analyses of the texture or orientation of the nerve fibers, or analyses of the reflectivity, retardance, or other optical properties of the NFL. Other types of images may be used to obtain anatomical contextual information in the lateral dimensions, such as size or lateral locations of blood vessels, size or shape of the ONH, distance between the ONH and the fovea, texture or orientation of the nerve fibers, or retardance or other optical properties of the NFL.

The location of blood vessels is related to the NFL thickness. The embryonic development of nerve fiber bundles and the supply of blood in these vessels follow similar growth development. Since the NFL thickness over time may change as a result of pathology, but blood vessel location is not expected to change, the location of blood vessels carries important information about inherent anatomical variation. [Hood, D. C., *IOVS* Vol. 48, No. 8, 3662-3668 (2007), Hood D. C. and Kardon, R. H. *Prog. Retin Eye Res.* 26(6): 688-710. (November 2007), Hood D C et al., *IOVS* 49: E-Abstract 3765 (2008).]

Similarly, the orientation of nerve fiber is not expected to change over time, while its thickness varies with age and eye function. The retinal nerve fiber layer (RNFL) exhibits substantial linear birefringence (U.S. Pat. No. 5,459,570, U.S.

Pat. No. 5,485,229) which is likely the result of form birefringence of the cylindrical cell structures of parallel axons of the nerve fiber bundles. This property provides a mechanism to assess the RNFL thickness by measuring total retardation in the light passing through the RNFL. Histological measurements validate the correlation between the magnitude of the retardation and the RNFL thickness. Typically, the thickness of the RNFL quantifies the viability of the nerve fiber layer. A normative database has been developed containing thickness distribution measurements for healthy retinas. Measurements of unhealthy eyes have also been collected and are used in a classifier. The normative database and the classifier can be used for diagnosis by classifying a subject as within normal limits or abnormal. In addition to comparing the measured retinal thickness distributions to the normative data, measured retinal thickness distributions can also be compared to previous measurements on the same eye taken during a previous visit. Comparison to the normative data is useful for diagnosis. Comparison to a previous measurement is useful for analyzing the change in retinal function over time. Comparison to another modality such as a visual field analysis is useful for confirmation of change and/or the detection of an abnormality.

Different data types require different comparisons. Two dimensional images are generally compared on a pixel-by-pixel basis. For instance, another measurement and means of displaying the RNFL health is the deviation map. A deviation map is created by analyzing a region about the optic disc and comparing it pixel-by-pixel to a normative database. The deviation map is the difference at each location between the normal thickness at the location and the actual measured thickness at the same location. While a location is nominally a point or pixel, it could also be an estimate over a region or area. This difference or deviation from normal is frequently displayed overlaid on a grayscale fundus image, orienting the viewer to the location as well as the magnitude of the deviation. The GDx™ scanning laser polarimeter produced by Carl Zeiss Meditec, Inc. provides such a deviation from normal map overlaid on a fundus image.

Data collected along a circle at a fixed radius from the optic nerve head, often called a circle scan, are generally compared on a point-by-point basis. However, when data along a circle scan is summarized, generally by averaging the data over a fixed region, then the summary is compared to another similar summary. For example, when the data along the Superior quadrant is averaged, that average data point is compared to another quantity of data averaged over a similar region, usually data averaged over the Superior quadrant. These comparison methods are currently used in existing glaucoma structural imaging products. The Superior, Nasal, Inferior and Temporal regions over which the summary is computed are fixed based on observations about the typical distribution of data. These quadrants are chosen because they appear to roughly correspond to regions that contain axons specific to certain regions of the retina.

Several known polarization techniques are available to map out the topography, thickness, and fiber orientation of the RNFL, such as scanning laser polarimetry (U.S. Pat. No. 5,787,890) (SLP) and polarization sensitive optical coherence tomography (U.S. Pat. No. 6,356,036, U.S. Pat. No. 6,927,860) (PS-OCT). The orientation of the nerve fibers is directly along the slow axis of birefringence (Dreher, A. W. et al., Applied Optics, 31, Iss. 19, 3730) so determining the orientation of the slow axis of birefringence at a distribution of points provides an orientation map of the nerve fiber bundles within the retina. Since the fast axis is perpendicular to the slow axis, determination of the fast axis direction is also sufficient to find the orientation of the fiber bundles within the retina.

Typically, examination systems calculate thickness measurements within an annulus centered on the ONH. For SLP, the inner diameter of the annulus is nominally about 2.4 mm and outer diameter is around 3.4 mm. For most OCT systems, the annulus is centered at a radius of about 3.4 mm, and the width of the annulus can vary from tens of microns to 1 mm, depending on the protocol. There are several known ways to display the thickness measurements. One known display is a line graph plotting thickness against assumed angle, where the angle commonly starts on the temporal side of the eye, continuing up around the annulus through the superior to the nasal and then down the inferior finally ending where it started on the temporal side of the eye. This graph is commonly called the TSNIT (temporal-superior-nasal-inferior-temporal) curve. The TSNIT curve is the underlying source of many of the measurements and statistics commonly used to measure the health of the retina. Some of these metrics and statistics are the average RNFL thickness, the standard deviation of that thickness, and the average thickness over a region, such as the temporal region. Since the right eye and left eye are separately measured and normal eyes tend to be approximately symmetric while disease commonly strikes one eye first, a metric measuring the similarity between the patient's left and right eye's TSNIT is also commonly used. There are many ways to use nerve fiber layer orientation information to add value to such metrics and displays.

The TSNIT curve is an appropriate tool for measuring the overall health of the retina. The orientation of the nerve fiber layer near the ONH is approximately normal to a circle centered on the ONH in most of the population and it is well demonstrated that portions of the nerve fiber layer passing through certain regions of the circle about the ONH service particular regions of the retina. Therefore, the thickness of the nerve fiber layer in a particular region is generally indicative of the overall health of the retina over an associated retinal region. It is one of the objects of this invention to improve this tool.

Currently, the primary methods for controlling TSNIT measurement repeatability are methods addressing the centering of the measurement circle optimally on the ONH, or methods for correcting the RNFL thickness measurement data for misalignment after data acquisition. The methods and means discussed here also account for anatomical differences within the normal population. Correctly compensating for these differences improves the sensitivity and specificity of the comparison with a normative database. Currently there is a large variation in normal TSNIT curves. It is the purpose of one aspect of this invention to reduce the variation in normal TSNIT curves. We accomplish this by normalizing the TSNIT curves of normal (healthy) eyes. Performing the same normalization on an eye being examined enables a comparison of the examined eye to normals which is both more sensitive and more specific.

While the description of the TSNIT graph above specified an annulus, other regions can be the basis for measurements. For example, a statistic computed over a regional map which is essentially triangular or trapezoidal in shape is, in some instances, more appropriate for analyzing a wedge defect. A collection of circles at various radii from the center of the ONH may be more appropriate than an annulus, in particular for an imaging system adapted for circle scans.

Figure 2:
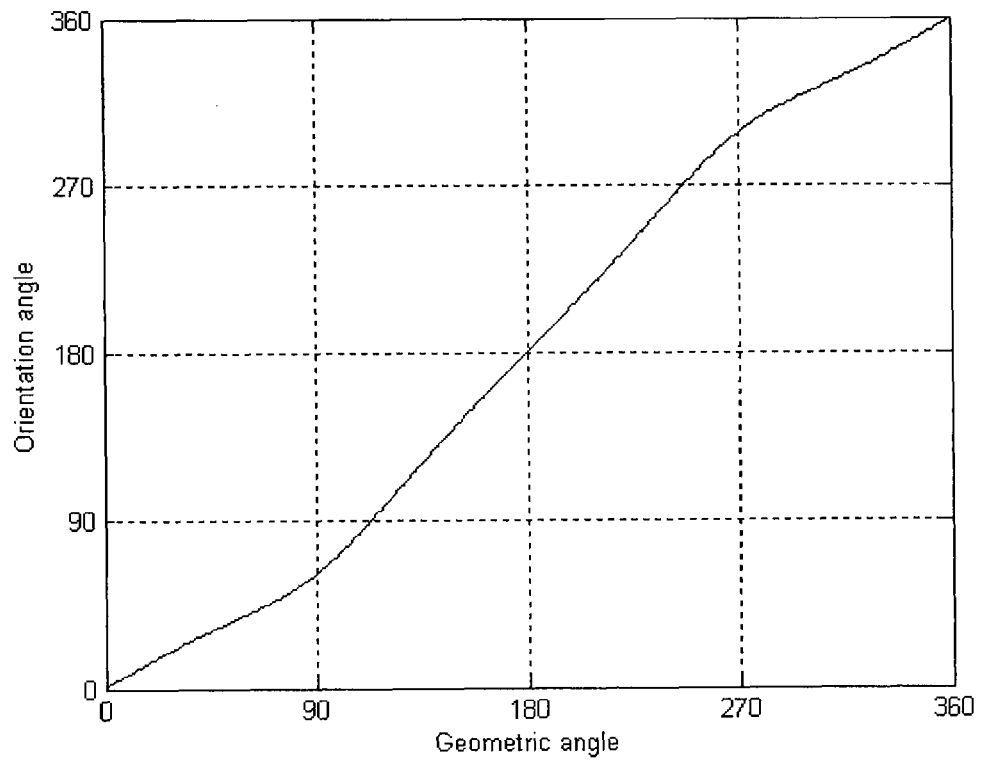
FIG. 2 is a plot of the alternate orientation of FIG. 1 versus the geometric angle.

An underlying assumption of current TSNIT measurements is that the nerve fiber bundles radially emanate from the ONH. Thus the nerve fiber thickness is associated with the orientation about the measurement circle by the location of the nerve fiber on the measurement circle. (Alternatively, one can say that the TSNIT is a map of the nerve fiber thickness at a position measured by the angle the measurement is taken on a circle scan.) FIG. 1 depicts the edge of the ONH 10. The dashed arrows 130 illustrate these radially directed bundles (or the angle of the location on the circle in polar co-ordinates.) While the nerve fiber bundles do not generally lie in exactly this orientation, it is a sufficiently accurate estimate to be useful for many comparisons. The current invention eschews the assumption that the nerve fiber bundles emanate radially from the ONH and instead uses measurements of the actual orientation, illustrated in FIG. 1 as measures along a circle scan 20 a short distance from the ONH 10, to improve thickness measurement comparisons. One such distribution of actual orientation vectors is illustrated by the solid arrows of FIG. 1, as indicated by 140. The dashed arrows are normal to the circle and their orientation measures the angle of the location from the horizontal. The orientation of the nerve fiber layer around the ONH provides a local coordinate system that is more anatomically significant than the geometric angle around the ONH. A measurement of this orientation over the retina allows us to map the nerve fiber bundle paths within the retina. The resulting curvilinear coordinate system is appropriate for improving the accuracy or reproducibility of RNFL measurements by well-known signal processing techniques such as smoothing, averaging or integrating along the nerve fiber bundles. This curvilinear coordinate system is also more appropriate for correlating RNFL measurements to other retinal exams, such as visual field testing, than coordinate systems based on the geometry of the retina. FIG. 2 is a plot of the fiber orientation angle versus the radial geometric angle of FIG. 1. This plot may have different shapes for different subjects. In FIG. 2, zero and 180 degree geometric angles correspond to the intersections of a horizontal line bisecting circle scan 20 while the 90 and 270 degree geometric angles correspond to the intersections of a vertical line bisecting the circle scan 20.

Figure 3:
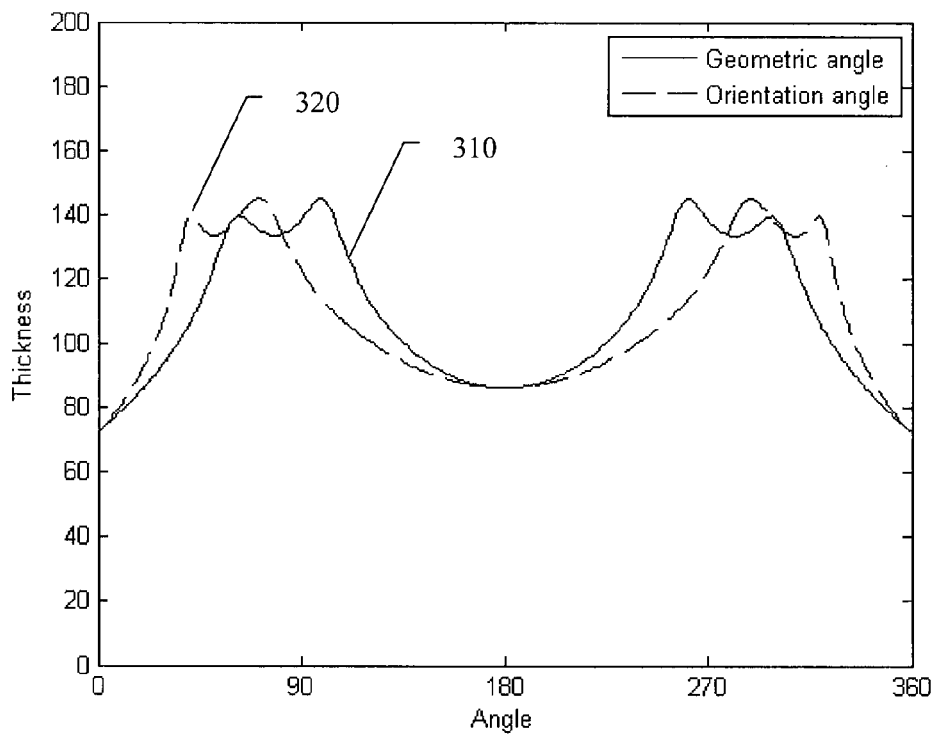
FIG. 3 is an example of a thickness plot where, in one instance the thickness is plotted as a function of the geometric angle and in another instance the thickness is plotted as a function of an orientation angle.

In one embodiment of the current invention, a modified TSNIT map displays the RNFL thickness measurement with respect to the orientation of the nerve fiber bundles. In the prior art display, the thickness, $t(r,\theta)$, at a point $(r,\theta)$ is displayed with respect to the geometric angle $\theta$ with vertex at the center of the ONH, as shown in FIG. 3 item 310. We acquire the thickness measurements $t(r,\theta)$ normally used in the TSNIT map and at the same locations $(r,\theta)$, we also acquire the orientation of the fiber bundle, $o(r,\theta)$. Instead of plotting $(\theta, t(r,\theta))$ for $\theta$ traversing $2\pi$ radians (360°) as has been done in prior art TSNIT maps, as shown in FIG. 3 item 320, we plot $(o(r,\theta), t(r,\theta))$. In this way, we have eliminated the individual variability of RNFL orientation from the map, presumably reducing the variability of measurements between individuals, and consequently reducing the variance in the distribution of "normal" eyes.

As an alternative, instead of plotting $(\theta, t(r,\theta))$ as has been displayed in prior TSNIT maps, we can plot $(\theta, t(r,o(r,\theta)))$, again reducing the variability of measurements between individuals. Of course, the thickness is not generally known at $(r,o(r,\theta))$, so the thickness displayed is the nearest neighbor thickness, an interpolated thickness value, or a thickness otherwise estimated from the thickness measurements that are available.

Figure 4A:
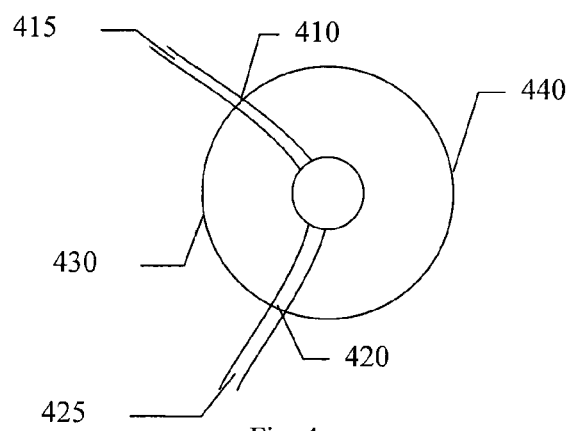
FIG. 4a illustrates a measurement region around the optic nerve head.
Figure 4B:
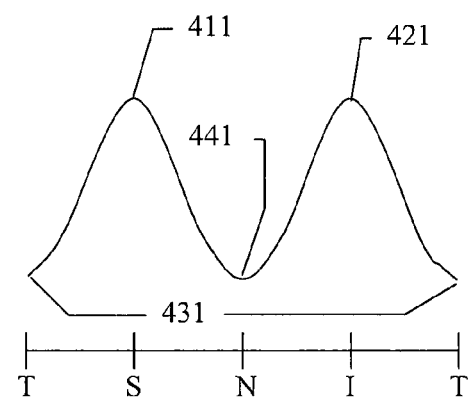
FIG. 4b illustrates a new TSNIT plot where the Superior and Inferior regions are determined from the measurement data.

More generally, we plot a function of the measured fiber tissue capacity against a function of the measured orientation. Even more generally, we plot a quantity related to the capacity of the fiber and computed from first measured parameters against a quantity related to the path of the fiber and computed from second measured parameters. One quantity related to the path of the fiber is the average fiber thickness over the Superior quadrant. This average can be computed using an estimate of the location of the Superior quadrant computed from measurements of blood vessels. The estimate of the quadrant location relies on the knowledge that major nerve fiber bundles follow essentially the same path as some major blood vessels. As illustrated in FIGS. 4a and 4b, the abscissa starts and ends at T, with equal partitions of S, N, and I, representing the 4 quadrants of the circle of radius 3.4 mm centered at the ONH. A blood vessel 415 associated with Superior quadrant nerve fibers is located and, even though the actual angular measure to this location is not 90°, the nerve fibers located nearest the blood vessel 410 are associated with label S at 411. Another blood vessel 425 associated with the Inferior quadrant nerve fibers is located and the nerve fiber located nearest this vessel 420 are associated with label I at 421. The location on the circle equal distance from this S and I and on the temporal side 430 is associated with label T at 431 while the location on the circle equal distance from this S and I and on the nasal side 440 is associated with label N at 441. Nerve tissue thickness is measured around the circle and warped between these fixed points to provide the TSNIT curve.

In FIG. 4a, a single blood vessel is associated with the Superior quadrant. Alternatively, the location associated with the Superior quadrant may be an aggregate position determined from a group of blood vessels. That is, a group of blood vessels can determine more than merely some location within the Superior quadrant, they can determine the entire quadrant. For example, the Superior quadrant may be defined as the region spanned by the largest blood vessel within 30° of vertical and neighboring large vessels within the superior hemisphere. Similarly, the Inferior quadrant location may be an aggregate position determined from a group of blood vessels within the Inferior hemisphere. In this sense, quadrant means only a quarter portion since these regions spanned by groups of blood vessels can be either larger or smaller than 90°. When the entire Superior quadrant and/or Inferior quadrant is identified, it is advantageous that the quadrant is rigidly remapped. Alternatively, warping the quadrant during remapping requires modification of the measurements within the quadrant to account for the warping.

Figure 5:
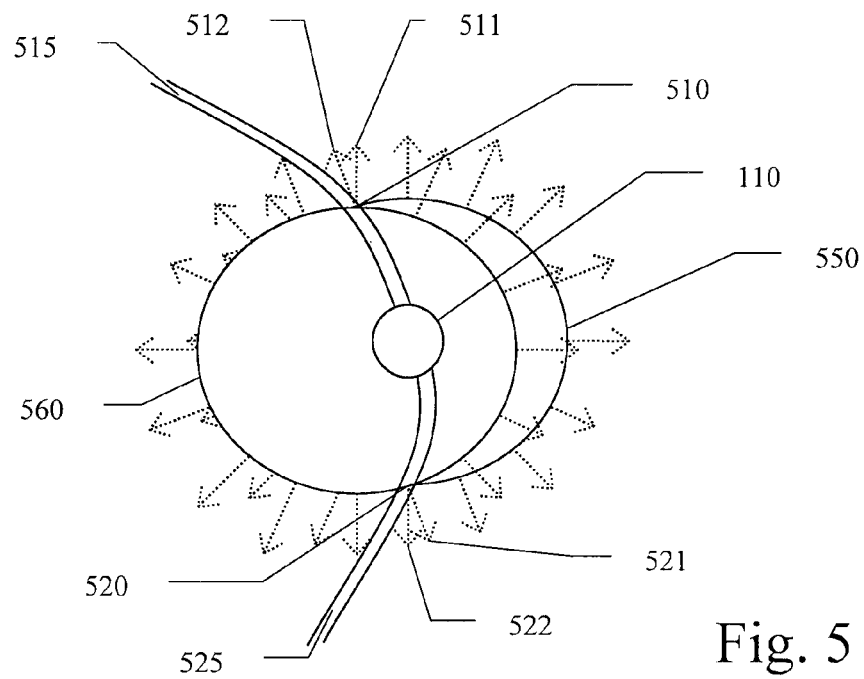
FIG. 5 illustrates differences in radial orientation between correctly positioned circle scan and an incorrectly placed circle scan.

This general technique also works to improve TSNIT curves when thickness measurements are acquired from a circle scan that is not optimally centered. FIG. 5 illustrates a correctly positioned circle scan 550, centered on the optic nerve head 110, and an incorrectly placed circle scan 560 which is not centered about the optic nerve head 110. Assuming again that the superior measurement corresponds to nerve fiber capacity located in the neighboring region of the blood vessel 515, the peak tissue thickness is measured at location 510 for both circle scans. The traditional TSNIT would place this measurement quite differently for circle scan 550 and circle scan 560, with the radial angle computed from normals 512 and 511, respectively. Indeed, in this illustration, the traditional TSNIT would associate the measurement 510 with the superior region for the improperly centered circle scan and place the measurement 510 distinctly apart from the superior region for the properly centered circle scan. For improved sensitivity and/or specificity, we want the peak tissue thickness to be aligned with the superior region. In this case, the off-centered circle scan actually produces a better result in the superior region than the properly centered circle scan, when using the traditional TSNIT measurement technique. Since the blood vessel tends to be associated with the peak, we are more likely to associate the superior region with the peak thickness in normal eyes when we use blood vessels or other anatomical data to determine the superior region. Thus, with either properly or improperly placed circle scans, associating the peak with the orientation associated with the blood vessel properly associates the peak with its superior region location, while the usual association, in this instance, provides a more correct association for the improperly placed circle scan than for the properly placed circle scan. Similarly, the inferior measurement corresponds to nerve fiber capacity located in the neighboring region of the blood vessel 525 and the peak tissue thickness in this region is measured at location 520 for both circle scans. Again, traditional TSNIT would place this measurement quite differently for circle scan 550 and circle scan 560, with the radial angle computed from normals 522 and 521, respectively. Unlike in the superior hemisphere, in this illustration, the traditional TSNIT would associate the measurement 520 with the inferior region for the properly centered circle scan and place the measurement 520 distinctly apart from the inferior region for the improperly centered circle scan. So, in this illustration, the properly centered circle scan does produce a better result in the inferior region than the off-centered circle scan, when the traditional TSNIT measurement technique is used to plot thickness measurements. Again, with either properly or improperly placed circle scans, associating the peak with the location of the blood vessel properly associates the peak with its inferior region location, while the usual association, in this instance, provides a more correct association for the properly placed circle scan than for the improperly placed circle scan. FIG. 5 illustrates that the anatomical identifier properly indicates the best locations to designate Superior and Inferior for improved TSNIT curves.

Using markers, such as blood vessels or fiber orientation, to identify the location of the superior and inferior regions, properly associates the thickness measurements with the appropriate locations. Use of such markers significantly reduces the impact of differences in anatomy and minor de-centering of the measurement circle on TSNIT curves.

When the partition between the superior hemisphere and inferior hemisphere can be identified, N and T of FIG. 4b should be associated with the nasal and temporal (respectively) intersections of the circle scan with the partition between superior and inferior hemispheres. The segments TS, SN, NI, and IT should be remapped separately, using linear interpolation whenever a better remapping based on analysis of the measurements and a priori information is not available.

In general, the capacity of the fiber to transmit information is a function of several parameters, including the thickness of the fiber layer and the compactness of the fiber packing. The orientation against which the capacity is plotted can be derived from the measurements of the fiber orientations, derived from anatomical information, or combinations of orientation and anatomical measurements. When nerve fiber thickness measurements are used to represent capacity, the thickness measurements may be weighted to compensate for variations in capacity per thickness for various regions of the eye as well as to compensate for compression or expansion of the orientation axis in the remapping. So the general form of the modified TSNIT plots a weighted, compensated capacity against a derived, warped orientation.

Figure 6:
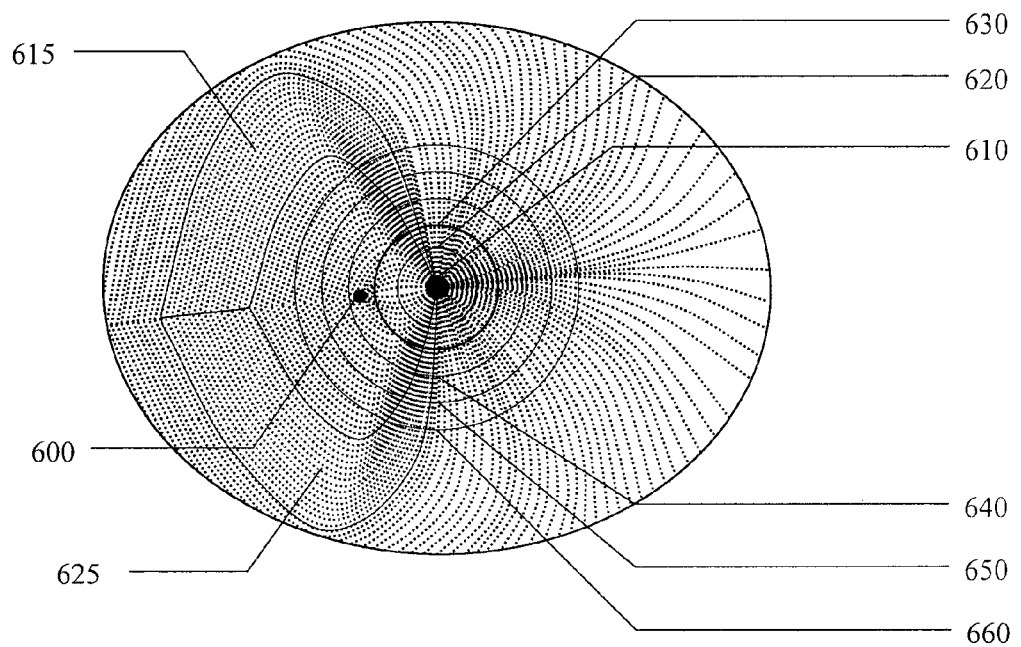
FIG. 6 illustrates tracing the path of the arcuate fiber bundles.

In another embodiment of the current invention, we show how to automatically compare the measured fiber bundles to a typical retinal map. The typical retinal map includes the typical orientation, $o_T(r,\theta)$, of the fiber bundles within the map. In FIG. 6, a schematic of the paths of fiber bundles in a typical eye are shown (based on Fitzgibbon and Taylor, J Comp Neur, 1996), along with circle scans 620, 630, 640, 650, and 660 centered about the optic nerve head 610. Also shown is the fovea 600. Starting with circle scan 620, the orientation of the fiber bundles is measured. Circle scan 630 should be placed sufficiently close to circle scan 620 so that the location of a bundle of interest can be determined on 630 from the known location and orientation on 620. In this way, a fiber bundle can be traced from the ONH to the retinal periphery. In this way, the superior arcuate fiber bundle 615 and inferior arcuate fiber bundle 625 can be automatically traced by tracking software running on a computer processing unit from the ONH to as far in the peripapillary region as the measurement system can measure.

The measurements need not be computed using circle scans. Clearly squares or other geometrical patterns can be used to acquire measurement data. Furthermore, the measurement region need not be closed or separate. A spiral pattern or sequence of arcs or lines could also be used. It is sufficient that the scan pattern be shaped so that the measurement data is adequate to map the fiber bundle.

Figure 7:
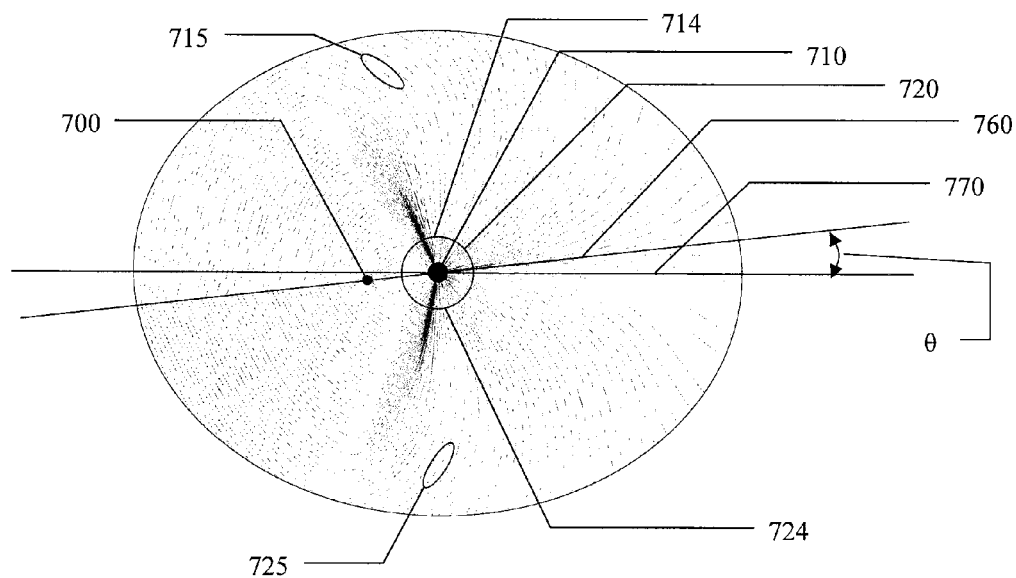
FIG. 7 illustrates a typical nerve fiber bundle map.
Figure 8:
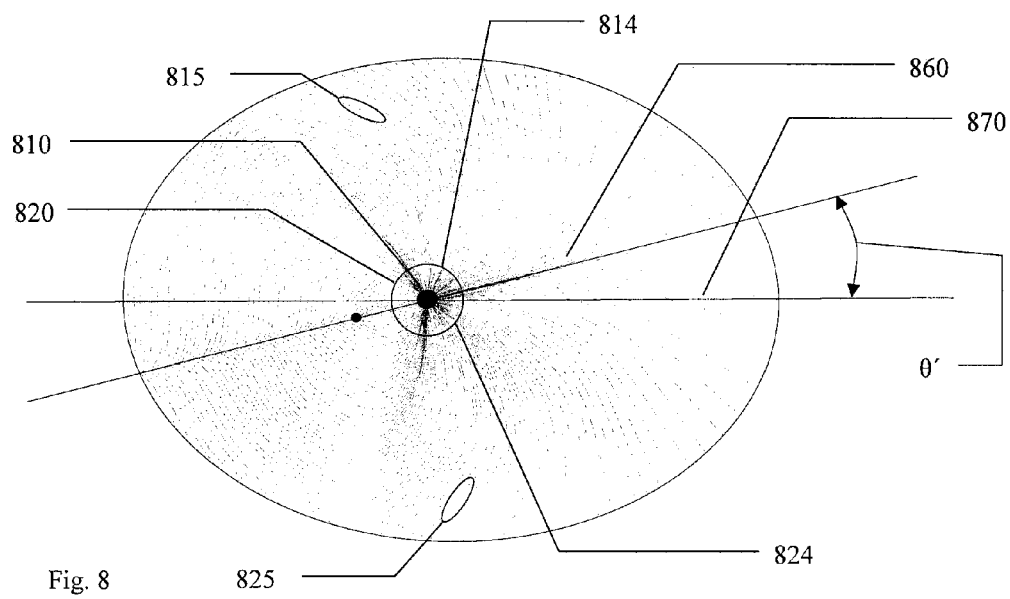
FIG. 8 illustrates a particular nerve fiber bundle map.

In a typical retinal fiber bundle map, a fiber bundle is associated with the regions of the retina that the fiber bundle services. This typical map can be theoretical or measured. Garway-Heath et al, (*Ophthalmology* 107 (10) 2000) mapped visual field points using high-resolution perimetry to positions on the optic nerve by choosing RNFL photographs with prominent nerve fiber bundles from an archive of RNFL images of subjects with localized defects in their visual acuity. The researchers manually traced an observed nerve fiber bundle in the photograph from the visual field defect back to the optic nerve, determining the location at the ONH of the defective bundle. This allowed them to develop a typical mapping of visual field points to the circumferential position of the origin of nerve fiber bundles at the optic nerve head. the current thickness measurements, $t(r,\theta)$, and orientation of the fiber bundle measurements, $o(r,\theta)$, at any point $(r,\theta)$ on the retinal surface are acquired, typically on a circle at some radius r, say $r_0$, near the ONH and compared to the typical map. The fiber bundles of the current measurements may be associated with the fiber bundles of the same orientation at the same $r_0$ in the typical orientation map or they may be associated with fiber bundles servicing the same region of the periphery. FIG. 7 illustrates a typical retinal fiber bundle map with locations 715 and 725 identified in the typical peripheral retina associated with locations 714 and 724, respectively, where the fiber bundle crosses the circle scan 720 on its way from the optic nerve head 710 to the peripheral retina. FIG. 8 illustrates a particular map with locations 815 and 825 identified in the particular peripheral retina associated with locations 814 and 824, respectively, where the fiber bundle crosses the circle scan 820 on its way from the optic nerve head 810 to the peripheral retina. After correction for anatomical difference in the typical and particular maps (such as the slope of the line through the ONH and fovea), regions 715 and 725 correspond approximately in location to regions 815 and 825, respectively. Tracing the fiber bundle paths in FIG. 7 back toward the ONH 10, we see that the path associated with fiber in region 725 intersects the circle scan 720 at location 724 and the path associated with fiber in region 715 intersects the circle scan 720 at location 714. Similarly, tracing the fiber bundle paths in FIG. 8 back toward the ONH 10', we see that the path associated with fiber in region 825 intersects the circle scan 820 at location 824 and the path associated with fiber in region 815 intersects the circle scan 820 at location 814. In this way, the association between 725 and 825 forms an association between 720 and 820. Similarly, the association between 715 and 815 forms an association between 714 and 814. Whether associated peripheral regions produce associated locations near the ONH or associated locations near the ONH produce associated peripheral regions is immaterial, the paths taken by the fiber bundles link specific locations near the ONH to their related peripheral regions and vice versa.

In this manner, fiber bundles of the current measurements near the ONH are associated with the regions of the retina that the fiber bundles service. Areas of decreased RNFL thickness thus predict regions of decreased retinal function. These regions of decreased retinal function can be correlated to other exams of the retina, such as visual field measurements.

In the typical fiber bundle illustration FIG. 7, the horizontal meridian 770 is at an angle θ of approximately 7° from the line 760 through the center of the fovea 700 and the center of the ONH 710. FIG. 7 uses the same typical fiber bundle map as FIG. 6. Whereas FIG. 6 illustrates the arcuate fiber bundle paths and a method for tracing a fiber bundle using orientation data, FIGS. 7 and 8 illustrate the use of a typical fiber bundle map for locating regions within the particular fiber bundle map once the typical and particular fiber bundle maps are linked. In the particular fiber bundle illustration FIG. 8, the horizontal meridian 870 is at an angle θ' of approximately 14° from the line 860 through the center of the fovea and the center of the ONH. The extreme angle θ' was used for illustrative purposes so that the differences between FIGS. 7 and 8 would be more easily discerned.

Specifically, a typical fiber bundle map $m_T$ is defined, thereby specifying the orientation $o_T(r,\theta)$ of the typical fiber bundles at various locations throughout the map. The path that the typical nerve fiber bundle takes is included in the map $m_T$. The path that a particular nerve fiber takes from the ONH to its terminal cell locations is determined in $m_T$ by its orientation $o_T(r,\theta)$ at the ONH. 715 and 725 are portions of the path taken by the nerve fiber bundles 714 and 724, respectively. The path $p(o_T(r_0,\theta))$ is the path of the nerve fiber with orientation $o_T(r,\theta)$ at the ONH, including its terminal cells. The measured orientation of the current fiber bundles whose thickness is being evaluated is $o(r_0,\theta)$. The associated region of cells serviced by this bundle is the region of terminal cells of $p(o(r_0,\theta))$. In this way, a region of reduced RNFL thickness, $t(r_0,\theta)$, is associated with the region of terminal cells of $p(o(r_0,\theta))$. The predicted decreased retinal function within this region of terminal cells can be correlated to other exams of the retina, such as visual field measurements.

Improvements are achieved by normalizing the typical fiber bundle map and the typical retinal map. Because of the variations in anatomy, actual fiber bundle maps vary substantially. However, these variations are diminished by abstracting the fiber bundle map into an anatomical function fiber bundle map. By associating the anatomical function fiber bundle map with an anatomical function retinal map, a perceived region of diminished capacity derived from the retinal measurements can be associated with a functional region of reduced visual field and vice-versa. In this way, measurements related to nerve fiber capacity for transmitting information (such as measurements of nerve fiber thickness, counts of the number of nerve fiber bundles, or measurements of the size of nerve fiber bundles) and measurements indicative of the portion of the retina serviced by the nerve fiber (such as fiber orientation near the ONH or fiber paths) are combined to provide metrics discerning overall and specific eye function.

In yet another embodiment of the current invention, we use the orientation of the nerve fiber bundles for post processing statistics. While this does not change the average thickness over all samples, it can have a significant impact on the average thickness over a region (such as samples over the superior or inferior regions.) For example, when computing the superior average thickness, the prior art methodology fixes a starting angle, say $\theta_0$, and an ending angle, say $\theta_N$, and then average over measurement samples $\theta_i$:

$$\frac{\sum_{\theta_0 \leq \theta_i \leq \theta_N} t(r,\theta_i)}{\sum_{\theta_0 \leq \theta_i \leq \theta_N} 1}.$$

In this embodiment of the present invention, the superior average thickness becomes:

$$\frac{\sum_{\theta_0 \leq o(r,\theta_i) \leq \theta_N} t(r,\theta_i)}{\sum_{\theta_0 \leq o(r,\theta_i) \leq \theta_N} 1}$$

where $o(r,\theta_i)$ is the orientation angle of the retinal fiber bundle at the polar coordinate $(r,\theta_i)$. While $\theta_0$ and $\theta_N$ here are ostensibly that θ previously chosen as a start and end angle, respectively, over which to average, clearly any nonoverlapping angles can be chosen for starting and ending the averaging procedure.

In general, for any remapping of the measurement parameters, we can compute statistics such as average, standard deviation, and variance over regions of interest. In some cases, statistical computations accommodate the remapping by computing the statistic over a changed region or by modifying the parameter used in the statistical computation. For example, if the angle subtended by the Superior quadrant is rigidly remapped, the Superior Average is computed in the usual way. However, if the Superior quadrant is remapped by means of a rotation and one or more stretches, then the Superior Average should account for both the change in the shape of the region, but also the change in density contributed by the stretching.

Historically, θ=0 was chosen to be the geometric horizontal line 770 through the ONH, 710 in FIG. 7. Clearly alternate choices are available. For example, one can choose the origin θ=0 to be the direction to the center of the fovea from the center of the ONH (or the opposite direction, 180° from the ONH to the fovea). The line 760 through the fovea 700 and the center of the ONH 710 essentially divides the RNFL into its physical superior and inferior hemispheres. The ocular hemispheres nominally divide the RNFL, with fiber bundles emanating from the ONH in the superior hemisphere generally remaining in the superior hemisphere until terminating in the peripheral retina and fiber bundles emanating from the ONH in the inferior hemisphere generally remaining in the inferior hemisphere until they too terminate in the peripheral retina. Typically the line through the fovea and the center of the ONH 760 lies approximately 8° from the horizontal 770, angle θ.

Thus, we can determine the nerve fiber layer orientation directly through measurements of the nerve fiber bundles, or indirectly by association with anatomical cues, such as by association with the major blood vessels of the retina. It is known that portions of the nerve fiber layer follow roughly the same orientation as the major blood vessels that service the retina. In particular, the superior and inferior directions may be associated with the major blood vessels extending more or less upward and downward, respectively, from the ONH. Additional orientations may be associated with additional blood vessels or assigned using intrinsic or extrinsic evidence or by interpolation or extrapolation.

For simplicity of exposition, we described a comparison with a single "typical map". Clearly, more than one typical map may be available and used for comparison, depending on local variations. For example, anatomical variations differ by race, shape of eyeball, or axis length variations of the ONH. Contextual information accounting for individual anatomical variations may be used to improve comparisons to normative databases. More than one "typical" eye type can provide a context for comparison of measurements to one or more normative database and/or one or more typical map.

Figure 9:
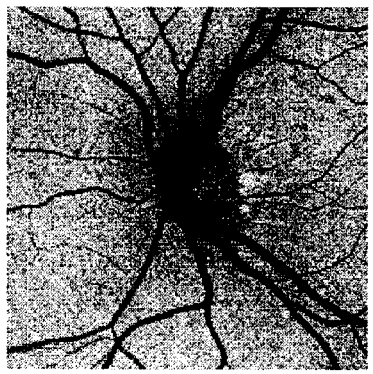
FIG. 9 illustrates an en-face image of the fundus, including blood vessels.
Figure 10:
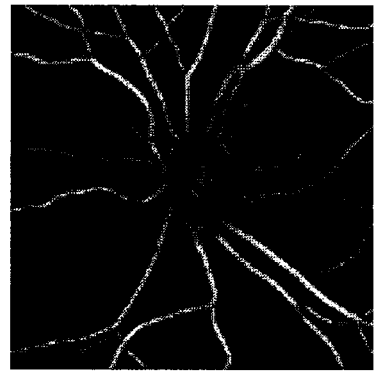
FIG. 10 illustrates a vessel enhanced image.
Figure 11:
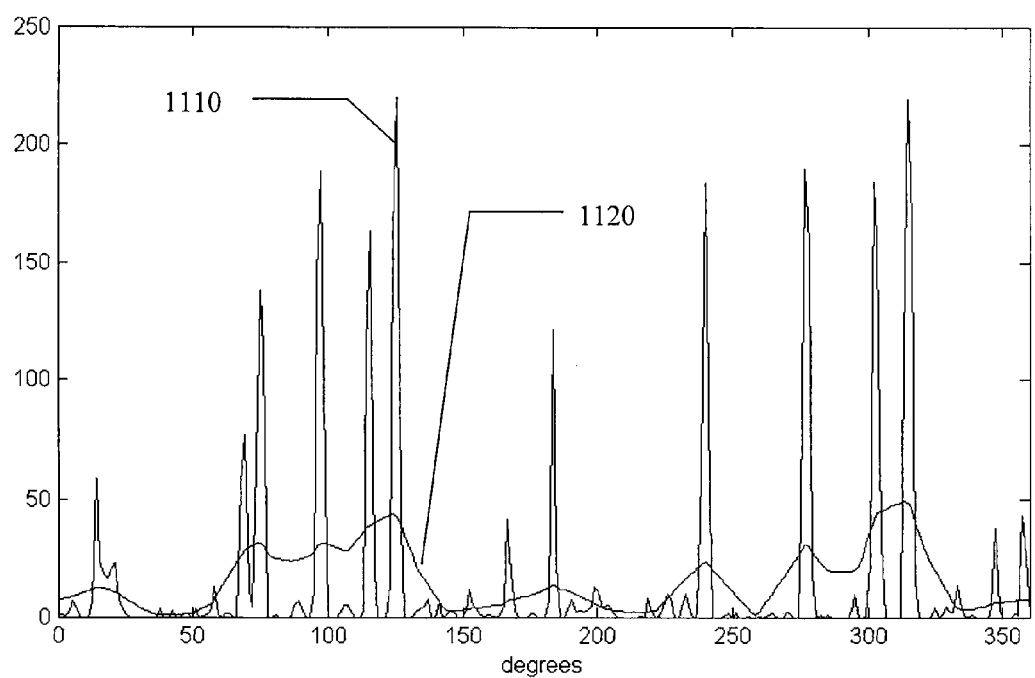
FIG. 11 illustrates a blood vessel likelihood map before and after smoothing.

Improved blood vessel detection is achieved by enhancing the vessels. An en-face image of the fundus or a full or partial axial projection of the OCT data [U.S. Pat. No. 7,301,644 issued to Knighton, et al] as shown in FIG. 9 can be processed to create a vessel-enhanced image as shown in FIG. 10 and described in co-pending U.S. Patent Publication 2008/0100612, which is hereby incorporated by reference. This technique for enhancing tubular regions was demonstrated by Frangi [in Frangi, A., et al., *IEEE Trans on Medical Imaging, Vol.* 18, No. 10, pp. 946-956 (1999)] and Sato [in Sato, Y., et al., *Medical Image Analysis,* 2(2):143-168 (1998)]. From this, we can estimate the likelihood of a blood vessel being located at each lateral location in the scan. The blood vessel likelihoods can then be extracted along the circular profile of the peripapillary scan. Convolving the blood vessel likelihood map with a broadening window allows us to associate similar blood vessel patterns based on the correlation or distance between the smoothed blood-vessel likelihood data. FIG. 11 shows the blood vessel likelihood map before smoothing 1110 and after smoothing 1120. The smoothed blood vessel likelihood map 1120 was computed using a triangular window. Certainly, other windows known to those versed in image processing could be used, such as a Hanning window, or a Gaussian window, etc.

Figure 12:
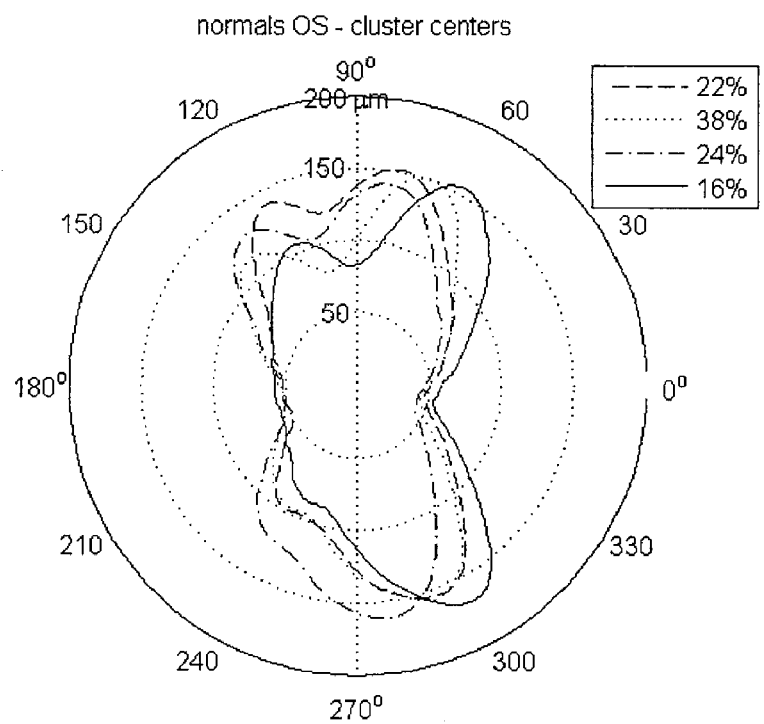
FIG. 12 illustrates a sample database clustered according to its patterns of NFL thickness around a peripapillary scan circle.

Partitioning the normative database can improve specificity and sensitivity. In one embodiment of the partitioning method, the normative database is partitioned using an unsupervised classification algorithm. FIG. 12 shows a sample database clustered according to its patterns of NFL thickness around a peripapillary scan circle using k-means clustering.

The patient being evaluated can then be assigned to a partition based on similarity of its NFL thickness profile to that of the clusters. In a preferred embodiment, the patient is categorized by the similarity of its blood vessel locations to the blood vessel locations of the clusters, although the clusters were originally partitioned on the basis of NFL thickness profiles. In yet another embodiment, the clusters may be originally partitioned on the basis of blood vessel locations and the patient categorized based on blood vessel locations.

In another embodiment of the partitioning method, the database of normals is partitioned using supervised classification, by selecting examples of anatomical variation in normals and partitioning the remainder of the normals database according to their similarity to these prototypes.

Figure 13:
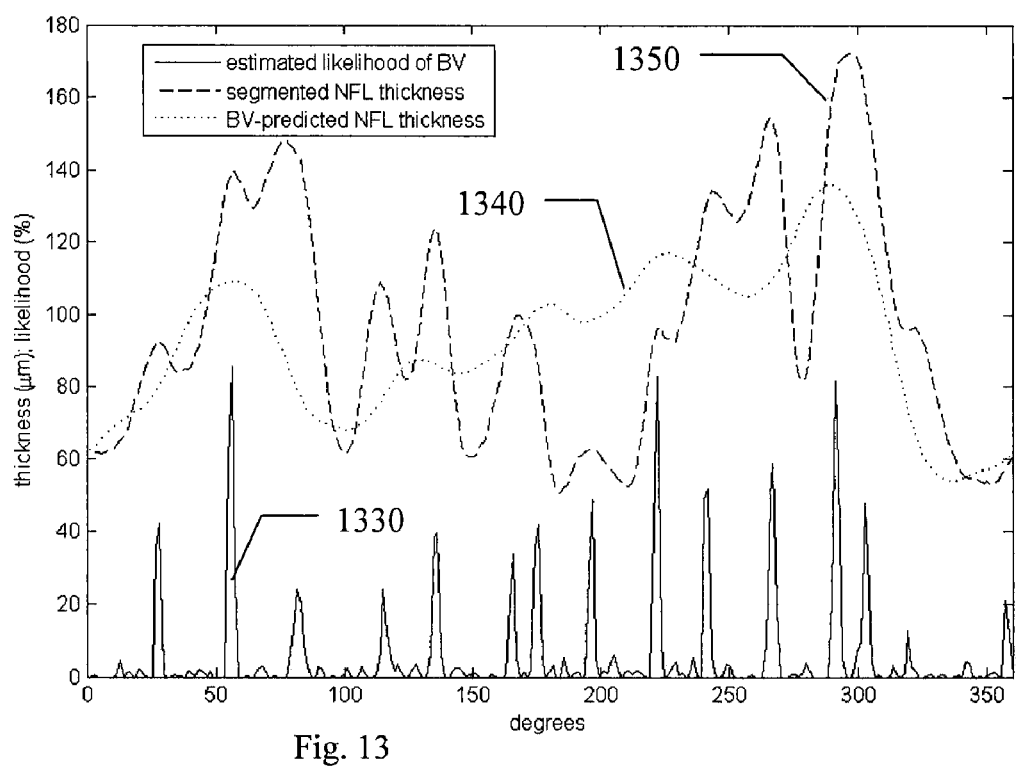
FIG. 13 illustrates a blood vessel likelihood map, a blood vessel likelihood estimate of the NFL thickness with thickness offset, and the actual OCT measurement of the NFL thickness.

One embodiment of the compensation method creates predictions of the NFL thickness based on blood vessel likelihood. This may be performed by convolving the blood vessel likelihood with an appropriate broadening function and adding a constant thickness offset to improve the prediction. FIG. 13 shows the blood vessel likelihood map 1330, the blood vessel likelihood estimate of the NFL thickness with thickness offset 1340, and the actual OCT measurement of the NFL thickness 1350. Here the window used for estimating NFL thickness from the blood vessel estimate is longer than the one previously discussed and a raised cosine window was used. The blood vessel likelihood function may alternatively be filtered, for example, by morphological operations such as erosion and dilation, order filters, logic-based filters, fuzzy logic filters, or skeletonization, prior to convolution with the broadening function. Other nonlinear processing, such as image thresholding, can be applied prior to NFL thickness prediction. Generally, these non-linear operations can be properly applied, with somewhat different results, at different points in the processing stream. For example, thresholds are generally applied to the image before dilation or erosion, so that binary versions of these operations can be applied. However, thresholds can again be applied after broadening. In one aspect of the invention, nonlinear processing is used to lower the relative influence of large vessels on the NFL prediction. If fundus images are available at wavelengths that distinguish between arteries and veins, e.g., near 700 nm, treating those vessels differently can improve NFL prediction. Alternate processing at different locations in the scan improves specificity by properly identifying characteristics within regions. For example, weighting the vessel likelihood more heavily in the superior and inferior regions, while decreasing the weight in the temporal and nasal regions can improve the comparison of the smoothed likelihood map with the NFL thickness in normal eyes. Similar improvement is expected with abnormals. Alternatively, post processing the predicted NFL thickness in a spatially varying manner can account for spatially varying influences of anatomical features or other contextual information. In one embodiment that predicts NFL thickness based on blood vessel likelihood, the predicted thicknesses are subtracted from the measured thicknesses, leaving a residual thickness. Normative limits and individual comparisons are then performed using these residual thicknesses.

Figure 14A:
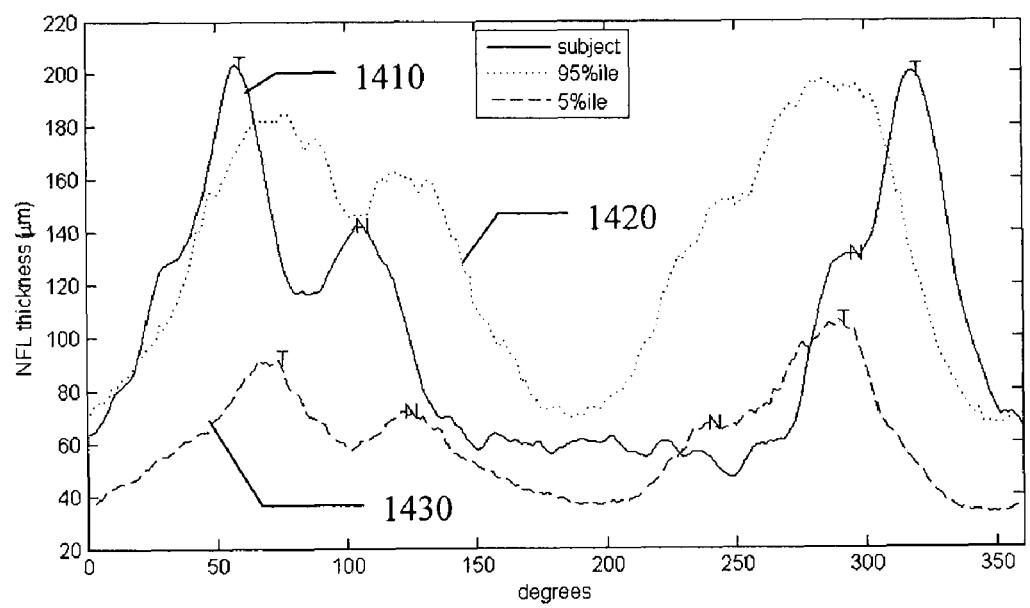
FIGS. 14a and b illustrates a remapping of the NFL measurements.
Figure 14B:
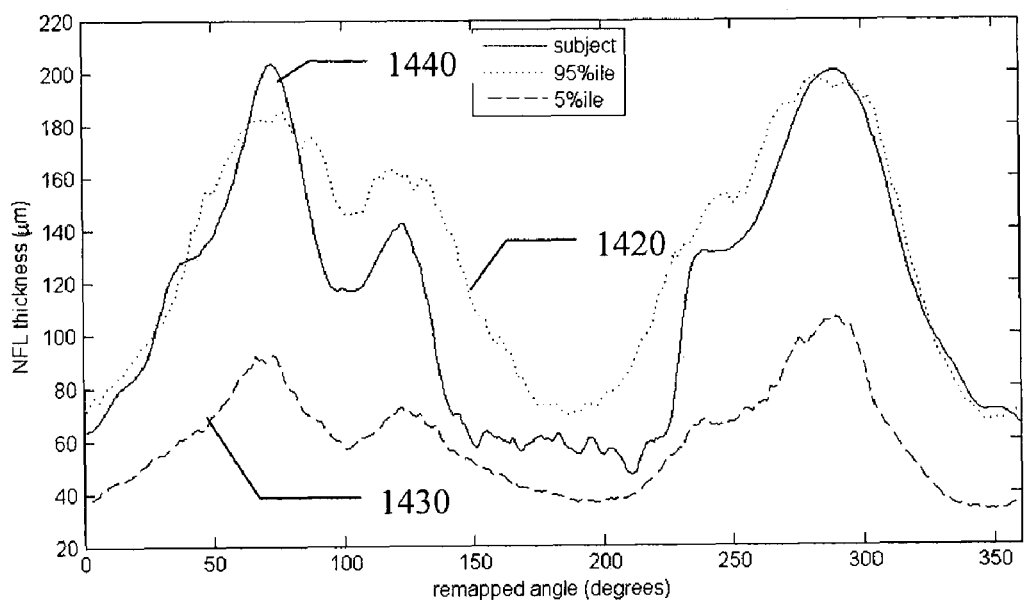

In one embodiment of the lateral mapping method, the angles of the peripapillary scan are remapped according to the orientation of the NFL at these points as described above. In another embodiment, the angles of the peripapillary scan are remapped according to the location of the major nerve fiber bundles. Peaks in the patient's measured NFL thickness are matched to nearby peaks in the normative limits, and the angles are linearly interpolated between the matched peak locations. FIG. 14*a* shows the direct measurement of the NFL thickness 1410 compared to the 95-th percentile of the normative database, 1420, and the 5-th percentile of the normative database, 1430. FIG. 14*b* shows the same measurement data remapped 1440. An alternate lateral mapping embodiment remaps the angles according to the peaks of the blood-vessel prediction of NFL thickness as described above.

Figure 15A:
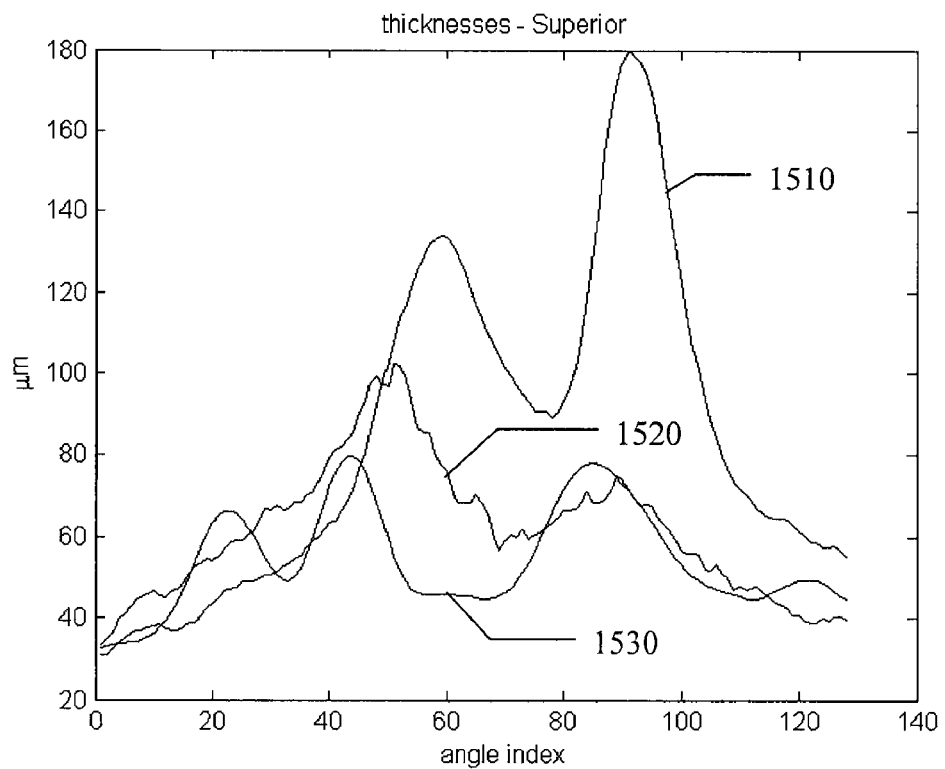
FIGS. 15a and b illustrates a sorting of the NFL measurements.
Figure 15B:
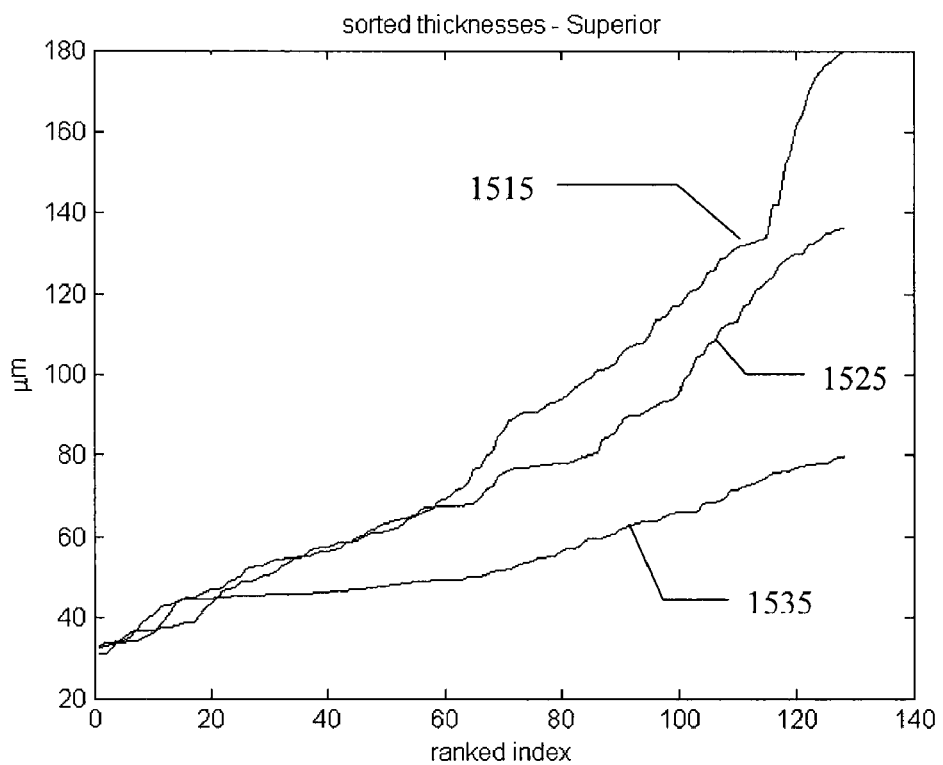

A variety of techniques may be employed to compare peaks in a patient's measured NFL thickness to peaks in the normative limits. These techniques may differ at different locations. One embodiment simply sorts the thickness values measured within a certain sector of the scan and uses these sorted values for establishing normative limits and performing individual comparisons to these limits. In FIG. 15*a*, the 128 measurements of the Superior half of a normal peripapillary scan 1510 are shown in comparison with the Superior half of the 5-th percentile of normal data 1520 and the Superior half of a glaucomatous eye 1530. FIG. 15*b* displays the data of curves 1510 and 1530 in sorted form, where the data for curve 1515 corresponds to 1510 and the data for curve 1535 corresponds to 1530. Curve 1525 represents the 5-th percentile of normal data after sorting each subject. Alternatively, a local maximum of the patient's measured NFL profile is calculated, to constrain the amount that a peak can be shifted to compare to the normative limits. In yet another embodiment a parametric fitting is performed to stretch and shrink regions of the angle axis to give a locally optimum fit of the data to the normative limits. Monitoring progression of health or of a disease can be realized by analyzing a parameter or a combination of parameters over time. RNFL thickness is a useful parameter for monitoring the progression of retinal health. In particular, RNFL thickness is a useful parameter for monitoring glaucoma progression analysis.

It should be understood that the embodiments, examples and descriptions have been chosen and described in order to illustrate the principals of the invention and its practical applications and not as a definition of the invention. Modifications and variations of the invention will be apparent to those skilled in the art. The scope of the invention is defined by the claims, which includes known equivalents and unforeseeable equivalents at the time of filing of this application.

The following references are hereby incorporated herein by reference.

US Patent Documents

U.S. Pat. No. 5,459,570, Swanson, et al., "Method and apparatus for performing optical measurements"

U.S. Pat. No. 5,485,229, Hare, "Method and apparatus for determining electrical activity in the retinal nerve fiber layer using intrinsic birefringent properties of retinal ganglion cell axons"

U.S. Pat. No. 5,787,890, Reiter, et al., "Eye examination apparatus employing polarized light probe"

U.S. Pat. No. 6,208,415, De Boer, et al., "Birefringence imaging in biological tissue using polarization sensitive optical coherent tomography"

U.S. Pat. No. 6,356,036, Zhou, "System and method for determining birefringence of anterior segment of a patient's eye"

U.S. Pat. No. 6,385,358 Everett et al. Birefringence insensitive optical coherence domain reflectometry system U.S. Pat. No. 6,927,860, Podoleanu, et al., "Optical mapping apparatus with optimized OCT configuration"

U.S. Pat. No. 7,016,048, Chen et al., "Phase-resolved functional optical coherence tomography: simultaneous imaging of the stokes vectors, structure, blood flow velocity, standard deviation and birefringence in biological samples"

U.S. Pat. No. 7,301,644, Knighton, et al., "Enhanced optical coherence tomography for anatomical mapping"

Other Publications

C. K. Hitzenberger, E. Gotzinger, M. Sticker, M. Pircher, and A. F. Fercher, "Measurement and imaging of birefringence and optic axis orientation by phase resolved polarization sensitive optical coherence tomography," 2001, Optics Express, Vol. 9, No. 13, 780-790

A. W. Dreher, Klaus Reiter and R. N. Weinreb, "Spatially Resolved Birefringence of the Retinal Nerve Fiber Layer Assessed With a Retinal Laser Ellipsometer," 1992, Applied Optics, Vol. 31, No. 19, 3730-3735

J. F. de Boer, T. E. Milner, J. S. Nelson, "Determination of the depth-resolved Stokes parameters of light backscattered from turbid media by use of polarization-sensitive optical coherence tomography," 1999, Optics Letters Vol. 24, 300-302.

A. Frangi, W. Niessen, R. Hoogeveen, T. van Walsum, and M. Viergever, "Model-based quantitation of 3D magnetic resonance angiographic images," IEEE Trans. Med. Imag., vol. 18, no. 10, pp. 946-956, October 1999.

T. Fitzgibbon and S. F. Taylor, "Retinotopy of the Human Retinal Nerve Fibre Layer and Optic Nerve Head," 1996, The Journal of Comparative Neurology, Vol. 375, 238-251

D. F. Garway-Heath, D. Poinoosawmy, F. W. Fitzke, R. A. Hitchings, "Mapping the Visual Field to the Optic Disc in Normal Tension Glaucoma Eyes," 2000, Ophthalmology Vol. 107, No. 10, 1809-1815

D. C. Hood, S. C. Anderson, M. Wall, and R. H. Kardon, "Structure versus Function in Glaucoma: An Application of a Linear Model," 2007, Invest. Ophthalmol. Vis. Sci. Vol. 48, No. 8, 3662-3668

Donald C. Hood and Randy H. Kardon, "A framework for comparing structural and functional measures of glaucomatous damage", Prog. Retin Eye Res. 26(6): 688-710. (November 2007)

D. C. Hood et al., "The Location of the Temporal Retinal Veins and Arteries Can Be Used to Improve the Sensitivity of the Retinal Nerve Fiber Layer Thickness Measured With Optical Coherence Tomography (OCT)", Invest. Ophthalmol. Vis. Sci. 49: E-Abstract 3765 (2008).

Jonas, J. B., Fernandez, M. C., Naumann, G. O., 1991. Parapapillary atrophy and retinal vessel diameter in nonglaucomatous optic nerve damage. Invest. Ophthalmol. Vis. Sci. 32, 2942-2947.

J B Jonas, M C Fernandez, "Shape of the neuroretinal rim and position of the central retinal vessels in glaucoma", British Journal of Ophthalmology, 78(2):99-102 (1994)

Rader, J., Feuer, W. J., Anderson, D. R., 1994. Peripapillary vasoconstriction in the glaucomas and the anterior ischemic optic neuropathies. Am. J. Ophthalmol. 117, 72-80.

J. E. Roth, J. A. Kozak, S. Yazdanfar, A. M. Rollins, J. A. Izatt, "Simplified method for polarization sensitive optical coherence tomography," 2001, Optics Letters Vol. 26, 1069-1071

Sato Y, Nakajima S, Shiraga N, Atsumi H, Yoshida S, Koller T, Gerig G, and Kikinis R, "Three dimensional multi-scale line filter for segmentation and visualization of curvilinear structures in medical images", Medical Image Analysis, 2(2): 143-168, 1998.

A. Waldock, M. Potts, J. Sparrow, and W. Karwatowski, "Clinical evaluation of scanning laser polarimetry: I. Intraoperator reproducibility and design of a blood vessel removal algorithm", British Journal of Ophthalmology, 82(3): 252-259. (March 1998)

J. B. MacQueen, "Some Methods for classification and Analysis of Multivariate Observations", Proceedings of 5-th Berkeley Symposium on Mathematical Statistics and Probability, Berkeley, University of California Press, 1:281-297 (1967).

What is claimed is:

1. A method for identifying a region of potentially reduced visual acuity in the eye comprising:
   obtaining a first set of measurements over a region associated with nerve fiber tissue in the eye, said measurements for characterizing the capacity or amount of the fiber tissue;
   obtaining a second set of measurements over said region associated with the nerve fiber tissue, said measurements for characterizing the orientation of nerve fibers or the orientation or position of anatomical features associated with the nerve fibers;
   determining from said first set of measurements at least one region of reduced tissue capacity or reduced amount of fiber tissue;
   identifying a region of potentially reduced visual acuity based on the location of the determined region of reduced tissue capacity or reduced amount of fiber tissue and an association between the second set of measurements and a map of fiber pathways; and
   displaying or storing information associated with the region of potentially reduced visual acuity.

2. A method as recited in claim 1, wherein the anatomical features associated with the nerve fibers are the retinal ganglion cells bodies associated with the axons that comprise the nerve fibers.

3. A method according to claim 1, wherein the first set of measurements is obtained using optical coherence tomography.

4. A method according to claim 1, wherein the first set of measurements includes measuring retinal nerve fiber thickness.

5. A method according to claim 1, wherein said reduced visual acuity is associated with a perimetry map.

6. A method of analyzing nerve fiber tissue of the eye using a database of normative data comprising:
   obtaining from a patient a first set of measurements over a region associated with the nerve fiber tissue, said measurements characterizing the capacity or amount of the fiber tissue;
   obtaining additional anatomical data from the eye of the patient, said additional anatomical data being independent of the nerve fiber tissue capacity or amount;
   selecting a subset of the normative database based on the anatomical data;
   comparing the patient measurements to the selected subset of the normative database; and
   displaying or storing information quantifying the comparison.

7. A method as recited in claim 6, wherein the anatomical data is obtained from an en-face image of the eye of the patient.

8. A method as recited in claim 6, wherein the subset of the normative database is selected using an unsupervised classification algorithm.

9. A method as recited in claim 6, wherein the subset of the normative database is selected using supervised classification.

10. A method of analyzing nerve fiber tissue of the eye comprising:
    obtaining a set of measurements over a region associated with the nerve fiber tissue, said measurements characterizing the capacity or amount of the fiber tissue;
    comparing the measurements to a normative database; and
    prior to the comparison step, modifying the set of measurements, the modification being a remapping of the data to account for anatomical variations; and
    storing or displaying information quantifying the comparison.

11. A method as recited in claim 10, wherein the remapping includes a parametric fit.

12. A method as recited in claim 10, wherein the remapping matches peak measurements to normative peaks and linearly interpolates between them.

13. A method as recited in claim 10, wherein the remapping includes sorting measurement values by magnitude within a region.

14. A method as recited in claim 13, wherein the region is selected from at least one of the temporal, superior, nasal, and inferior regions of the eye.

15. A method of analyzing nerve fiber tissue of the eye comprising:
    obtaining a set of measurements over a region associated with the nerve fiber tissue, said measurements characterizing the capacity or thickness of fiber tissue;
    modifying at least one of the measurements based on anatomical information to account for anatomical variations, wherein the modification is a remapping of the data; and
    displaying or storing the modified measurement data.

16. A method as recited in claim 15, wherein the remapping includes a parametric fit.

17. A method as recited in claim 15, wherein the remapping matches peak measurements to normative peaks and linearly interpolates between them.

18. A method as recited in claim 15, wherein the remapping includes sorting measurement values by magnitude within a region of the scan.

19. A method as recited in claim 18, wherein the region is selected from at least one of the temporal, superior, nasal, and inferior regions of the eye.

20. A method of analyzing nerve fiber tissue of the eye comprising:
    obtaining a set of measurements over a region associated with the nerve fiber tissue, said measurements characterizing the capacity or thickness of fiber tissue;
    modifying at least one of the measurements based on anatomical information to account for anatomical variations; and
    displaying or storing the modified measurement data wherein said step of modifying the measurements accounts for one of age, sex, or ethnicity, in addition to the anatomical information.

21. A method of analyzing nerve fiber tissue of the eye comprising:
    obtaining a set of measurements over a region associated with the nerve fiber tissue, said measurements characterizing the capacity or thickness of fiber tissue;
    modifying at least one of the measurements based on anatomical information to account for anatomical variations; and
    displaying or storing the modified measurement data wherein said anatomical information is selected from the group consisting of blood vessel size and blood vessel location.

22. A method of analyzing nerve fiber tissue of the eye comprising:
    obtaining a set of measurements over a region associated with the nerve fiber tissue, said measurements characterizing the capacity or thickness of fiber tissue;
    modifying at least one of the measurements based on anatomical information to account for anatomical variations; and
    displaying or storing the modified measurement data, wherein said anatomical information is obtained from an en-face image of the patient's eye.

23. A method as recited in claim 22, further comprising:
    estimating the locations of blood vessels from the en-face image; and
    predicting a distribution of nerve fiber thickness based on the estimated location of the blood vessels; and
    using this predicted nerve fiber thickness to modify the measurement data.

24. A method as recited in claim 23, wherein the prediction of nerve fiber thickness includes applying a broadening function to the estimated blood vessel locations.

25. A method as recited in claim 23, wherein the prediction of nerve fiber thickness uses a plurality of different processing techniques, each specialized for a particular region of the eye.

* * * * *

UNITED STATES PATENT AND TRADEMARK OFFICE
CERTIFICATE OF CORRECTION

PATENT NO. : 8,128,229 B2
APPLICATION NO. : 12/859727
DATED : March 6, 2012
INVENTOR(S) : Scott A. Meyer et al.

It is certified that error appears in the above-identified patent and that said Letters Patent is hereby corrected as shown below:

In column 1, line 41, delete "(TOP);" and insert -- (IOP); --, therefor.

In column 7, line 48, delete "0" and insert -- $\theta$ --, therefor.

In column 10, line 33, delete "the" and insert -- The --, therefor.

In column 17, line 3, in claim 2, delete "cells" and insert -- cell --, therefor.

Signed and Sealed this
Twenty-fifth Day of September, 2012

David J. Kappos
*Director of the United States Patent and Trademark Office*